United States Patent
Parodi et al.

(10) Patent No.: US 6,540,712 B1
(45) Date of Patent: Apr. 1, 2003

(54) METHODS AND LOW PROFILE APPARATUS FOR REDUCING EMBOLIZATION DURING TREATMENT OF CAROTID ARTERY DISEASE

(75) Inventors: Juan Carlos Parodi, Buenos Aires (AR); Takao Ohki, New York, NY (US)

(73) Assignee: Arteria Medical Science, Inc., San Francisco, CA (US)

(*) Notice: Subject to any disclaimer, the term of this patent is extended or adjusted under 35 U.S.C. 154(b) by 0 days.

(21) Appl. No.: 09/528,569

(22) Filed: Mar. 20, 2000

Related U.S. Application Data (63) Continuation-in-part of application No. 09/333,074, filed on Jun. 14, 1999, which is a continuation-in-part of application No. PCT/US99/05469, filed on Mar. 12, 1999, which is a continuation-in-part of application No. 09/078,263, filed on May 13, 1998.

(30) Foreign Application Priority Data

Mar. 12, 1999 (AR) .......................... 98 01 01146

(51) Int. Cl.[7] .............................................. A61M 37/00
(52) U.S. Cl. ..................................... 604/6.14; 604/5.01
(58) Field of Search ........................ 604/500, 509, 604/101.01, 103.09, 170, 104, 96.01, 103.07, 5.01, 6.09, 6.14, 27, 4.01; 606/127, 108, 159, 191, 192, 194, 195, 198, 200, 213

(56) References Cited

U.S. PATENT DOCUMENTS

| | | |
|---|---|---|
| 4,575,371 A | 3/1986 | Nordqvist et al. |
| 4,781,681 A | 11/1988 | Sharrow et al. |
| 4,794,928 A | 1/1989 | Kletschka ................. 128/344 |
| 4,921,478 A | 5/1990 | Solano et al. .............. 604/53 |
| 5,011,488 A | 4/1991 | Ginsburg |
| 5,102,415 A | 4/1992 | Guenther et al. |
| 5,478,309 A | * 12/1995 | Sweezer et al. ....... 604/101.04 |
| 5,549,626 A | 8/1996 | Miller et al. |
| 5,558,644 A | * 9/1996 | Boyd et al. ............ 604/102.02 |
| 5,584,803 A | 12/1996 | Stevens et al. |
| 5,669,927 A | 9/1997 | Boebel et al. |
| 5,738,652 A | * 4/1998 | Boyd et al. .................... 604/28 |
| 5,765,568 A | * 6/1998 | Sweezer et al. ............ 128/898 |
| 5,766,151 A | 6/1998 | Valley et al. |
| 5,794,629 A | 8/1998 | Frazee |
| 5,800,375 A | * 9/1998 | Sweezer et al. ....... 604/101.05 |
| 5,810,757 A | * 9/1998 | Sweezer et al. ............ 604/523 |
| 5,833,650 A | 11/1998 | Imran ......................... 604/53 |
| 5,895,399 A | 4/1999 | Barbut et al. |
| 5,916,193 A | 6/1999 | Stevens et al. |
| 5,925,016 A | 7/1999 | Chornenky et al. |
| 5,997,557 A | 12/1999 | Barbut et al. |
| 6,013,085 A | 1/2000 | Howard |
| 6,027,476 A | 2/2000 | Sterman et al. |
| 6,029,671 A | 2/2000 | Stevens et al. |

(List continued on next page.)

FOREIGN PATENT DOCUMENTS

EP    0 427 429 A2    5/1991    .......... A61M/25/10

*Primary Examiner*—Brian L. Casler
*Assistant Examiner*—Kevin C. Sirmons
(74) *Attorney, Agent, or Firm*—Fish & Neave; Nicola A. Pisano

(57) ABSTRACT

Methods and apparatus are provided for removing emboli during an angioplasty, stenting or surgical procedure comprising a catheter having an occlusion element, an aspiration lumen, and a blood outlet port in communication with the lumen, a guide wire having a balloon, a venous return catheter with a blood inlet port, and tubing that couples the blood outlet port to the blood inlet port. A blood filter and/or flow control valve may be included in-line with the tubing to filter emboli from blood reperfused into the patient and to control the degree of flow reversal.

19 Claims, 5 Drawing Sheets

U.S. PATENT DOCUMENTS

| | | |
|---|---|---|
| 6,042,559 A | 3/2000 | Dobak, III |
| 6,090,096 A * | 7/2000 | St. Goar et al. ............... 600/18 |
| 6,129,708 A | 10/2000 | Enger |
| 6,180,059 B1 | 1/2001 | Divino et al. |
| 6,228,052 B1 | 5/2001 | Pohndorf |
| 6,295,989 B1 | 10/2001 | Connors, III |
| 6,379,373 B1 * | 4/2002 | Sawhney et al. ............ 606/193 |
| 6,398,752 B1 * | 6/2002 | Sweezer et al. ............ 128/898 |

* cited by examiner

METHODS AND LOW PROFILE APPARATUS FOR REDUCING EMBOLIZATION DURING TREATMENT OF CAROTID ARTERY DISEASE

REFERENCE TO RELATED APPLICATION

The present application is a continuation-in-part of U.S. patent application Ser. No. 09/333,074, filed Jun. 14, 1999, which is a continuation-in-part of International Application PCT/US99/05469, filed Mar. 12, 1999, which is a continuation-in-part of U.S. patent application Ser. No. 09/078,263, filed May 13, 1998.

FIELD OF THE INVENTION

This invention relates to apparatus and methods for protecting against embolization during vascular interventions, such as carotid artery angioplasty and endarterectomy. More particularly, the apparatus and methods of the present invention induce controlled retrograde flow through the internal carotid artery during an interventional procedure, without significant blood loss.

BACKGROUND OF THE INVENTION

Carotid artery stenoses typically manifest in the common carotid artery, internal carotid artery or external carotid artery as a pathologic narrowing of the vascular wall, for example, caused by the deposition of plaque, that inhibits normal blood flow. Endarterectomy, an open surgical procedure, traditionally has been used to treat such stenosis of the carotid artery.

An important problem encountered in carotid artery surgery is that emboli may be formed during the course of the procedure, and these emboli can rapidly pass into the cerebral vasculature and cause ischemic stroke.

In view of the trauma and long recuperation times generally associated with open surgical procedures, considerable interest has arisen in the endovascular treatment of carotid artery stenosis. In particular, widespread interest has arisen in transforming interventional techniques developed for treating coronary artery disease, such as angioplasty and stenting, for use in the carotid arteries. Such endovascular treatments, however, are especially prone to the formation of emboli.

Such emboli may be created, for example, when an interventional instrument, such as a guide wire or angioplasty balloon, is forcefully passed into or through the stenosis, as well as after dilatation and deflation of the angioplasty balloon or stent deployment. Because such instruments are advanced into the carotid artery in the same direction as blood flow, emboli generated by operation of the instruments are carried directly into the brain by antegrade blood flow.

Stroke rates after carotid artery stenting have widely varied in different clinical series, from as low as 4.4% to as high as 30%. One review of carotid artery stenting including data from twenty-four major interventional centers in Europe, North America, South America and Asia, had a combined initial failure and combined mortality/stroke rate of more than 7%. Cognitive studies and reports of intellectual changes after carotid artery stenting indicate that embolization is a common event causing subclinical cerebral damage.

Several previously known apparatus and methods attempt to remove emboli formed during endovascular procedures by trapping or suctioning the emboli out of the vessel of interest. These previously known systems, however, provide less than optimal solutions to the problems of effectively removing emboli.

Solano et al. U.S. Pat. No. 4,921,478 describes cerebral angioplasty methods and devices wherein two concentric shafts are coupled at a distal end to a distally-facing funnel-shaped balloon. A lumen of the innermost shaft communicates with an opening in the funnel-shaped balloon at the distal end, and is open to atmospheric pressure at the proximal end. In use, the funnel-shaped balloon is deployed proximally (in the direction of flow) of a stenosis, occluding antegrade flow. An angioplasty balloon catheter is passed through the innermost lumen and into the stenosis, and then inflated to dilate the stenosis. The patent states that when the angioplasty balloon is deflated, a pressure differential between atmospheric pressure and the blood distal to the angioplasty balloon causes a reversal of flow in the vessel that flushes any emboli created by the angioplasty balloon through the lumen of the innermost catheter.

While a seemingly elegant solution to the problem of emboli removal, several drawbacks of the device and methods described in the Solano et al. patent seem to have lead to abandonment of that approach. Chief among these problems is the inability of that system to generate flow reversal during placement of the guide wire and the angioplasty balloon across the stenosis. Because flow reversal does not occur until after deflation of the angioplasty balloon, there is a substantial risk that any emboli created during placement of the angioplasty balloon will travel too far downstream to be captured by the subsequent flow reversal. It is expected that this problem is further compounded because only a relatively small volume of blood is removed by the pressure differential induced after deflation of the angioplasty balloon.

Applicant has determined another drawback of the method described in the Solano patent: deployment of the funnel-shaped balloon in the common carotid artery ("CCA") causes reversal of flow from the external carotid artery ("ECA") into the internal carotid artery ("ICA"), due to the lower flow impedance of the ICA. Consequently, when a guide wire or interventional instrument is passed across a lesion in either the ECA or ICA, emboli dislodged from the stenosis are introduced into the blood flow and carried into the cerebral vasculature via the ICA.

The insufficient flow drawback identified for the system of the Solano patent is believed to have prevented development of a commercial embodiment of the similar system described in EP Publication No. 0 427 429. EP Publication No. 0 427 429 describes use of a separate balloon to occlude the ECA prior to crossing the lesion in the ICA. However, like Solano, that publication discloses that flow reversal occurs only when the dilatation balloon in the ICA is deflated.

Chapter 46 of *Interventional Neuroradiology: strategies and practical techniques* (J. J. Connors & J. Wojak, 1999), published by Saunders of Philadelphia, Pa., describes use of a coaxial balloon angioplasty system for patients having proximal ICA stenoses. In particular, a small, deflated occlusion balloon on a wire is introduced into the origin of the ECA, and a guide catheter with a deflated occlusion balloon is positioned in the CCA just proximal to the origin of the ECA. A dilation catheter is advanced through a lumen of the guide catheter and dilated to disrupt the stenosis. Before deflation of the dilation catheter, the occlusion balloons on the guide catheter and in the ECA are inflated to block antegrade blood flow to the brain. The dilation balloon then is deflated, the dilation catheter is removed, and blood is aspirated from the ICA to remove emboli.

Applicant has determined that cerebral damage still may result from the foregoing previously known procedure; which is similar to that described in EP Publication No. 0 427 429, except that the ICA is occluded prior to the ECA. Consequently, both of these previously known systems and methods suffer from the same drawback—the inability to generate flow reversal at sufficiently high volumes during placement of the guide wire and dilation catheter across the stenosis. Both methods entail a substantial risk that any emboli created during placement of the balloon will travel too far downstream to be captured by the flow reversal.

Applicants note, irrespective of the method of aspiration employed with the method described in the foregoing *Interventional Neuroradiology* article, substantial drawbacks are attendant. If, for example, natural aspiration is used (i.e., induced by the pressure gradient between the atmosphere and the artery), then only a relatively small volume of blood is expected to be removed by the pressure differential induced after deflation of the angioplasty balloon. If, on the other hand, an external pump is utilized, retrieval of these downstream emboli may require a flow rate that cannot be sustained for more than a few seconds, resulting in insufficient removal of emboli.

Furthermore, with the dilation balloon in position, the occlusion balloons are not inflated until after inflation of the dilation balloon. Microemboli generated during advancement of the dilation catheter into the stenosed segment may therefore be carried by retrograde blood flow into the brain before dilation, occlusion, and aspiration are even attempted.

A still further drawback of both the device in EP Publication No. 0 427 429 and the *Interventional Neuroradiology* device is that, if they are used for placing a stent in the ICA instead of for ICA angioplasty, the stent often extends beyond the bifurcation between the ECA and the ICA. The occlusion balloon placed by guide wire in the ECA may snag the stent during retrieval. Emergency surgery then may be required to remove the balloon.

Imran U.S. Pat. No. 5,833,650 describes a system for treating stenoses that comprises three concentric shafts. The outermost shaft includes a proximal balloon at its distal end that is deployed proximal of a stenosis to occlude antegrade blood flow. A suction pump then draws suction through a lumen in the outermost shaft to cause a reversal of flow in the vessel while the innermost shaft is passed across the stenosis. Once located distal to the stenosis, a distal balloon on the innermost shaft is deployed to occlude flow distal to the stenosis. Autologous blood taken from a femoral artery using an extracorporeal blood pump is infused through a central lumen of the innermost catheter to provide continued antegrade blood flow distal to the distal balloon. The third concentric shaft, which includes an angioplasty balloon, then is advanced through the annulus between the innermost and outermost catheters to dilate the stenosis.

Like the device of the Solano patent, the device of the Imran patent appears to suffer the drawback of potentially dislodging emboli that are carried into the cerebral vasculature. In particular, once the distal balloon of Imran's innermost shaft is deployed, flow reversal in the vasculature distal to the distal balloon ceases, and the blood perfused through the central lumen of the innermost shaft establishes antegrade flow. Importantly, if emboli are generated during deployment of the distal balloon, those emboli will be carried by the perfused blood directly into the cerebral vasculature, and again pose a risk of ischemic stroke. Moreover, there is some evidence that reperfusion of blood under pressure through a small diameter catheter may contribute to hemolysis and possible dislodgment of emboli.

In applicant's co-pending U.S. patent application Ser. No. 09/333,074, filed Jun. 14, 1999, which is incorporated herein by reference, applicant described the use of external suction to induce regional reversal of flow. That application further described that intermittently induced regional flow reversal overcomes the drawbacks of naturally-aspirated systems such as described hereinabove. However, the use of external suction may in some instances result in flow rates that are too high to be sustained for more than a few seconds. In addition, continuous use of an external pump may result in excessive blood loss, requiring infusion of non-autologous blood and/or saline that causes hemodilution, reduced blood pressure, or raises related safety issues.

In view of these drawbacks of the previously known emboli removal systems, it would be desirable to provide methods and apparatus for removing emboli from within the carotid arteries during interventional procedures, such as angioplasty or carotid stenting, that reduce the risk that emboli are carried into the cerebral vasculature.

It also would be desirable to provide methods and apparatus for removing emboli from within the carotid arteries during interventional procedures, such as angioplasty or carotid stenting, that provide controlled retrograde blood flow from the treatment zone, thereby reducing the risk that emboli are carried into the cerebral vasculature.

It further would be desirable to provide emboli removal methods and apparatus that prevent the development of reverse flow from the ECA and antegrade into the ICA once the CCA has been occluded, thereby enhancing the likelihood that emboli generated by a surgical or interventional procedure are effectively removed from the vessel.

It still further would be desirable to provide an occlusion balloon on a guide wire for placement in the ECA during stenting of the ICA that mitigates the risk of snagging the stent during removal.

It also would be desirable to provide methods and apparatus for removing emboli during a carotid stenting procedure that enable filtering of emboli and reduced blood loss.

SUMMARY OF THE INVENTION

In view of the foregoing, it is an object of this invention to provide methods and apparatus for removing emboli from within the carotid arteries during interventional procedures, such as angioplasty or carotid stenting, that reduce the risk that emboli are carried into the cerebral vasculature.

It also is an object of the present invention to provide methods and apparatus for removing emboli from within the carotid arteries during interventional procedures, such as angioplasty or carotid stenting, that provide controlled retrograde blood flow from the treatment zone, thereby reducing the risk that emboli are carried into the cerebral vasculature.

It is another object of the present invention to provide emboli removal methods and apparatus that prevent the development of reverse flow between the ECA and ICA once the common carotid artery has been occluded, thereby enhancing the likelihood that emboli generated by a surgical or interventional procedure are effectively removed from the vessel.

It is a further object of this invention to provide methods and apparatus for an occlusion balloon on a guide wire for placement in the ECA during stenting of the ICA that mitigates the risk of snagging the stent during removal.

It is yet another object of the present invention to provide methods and apparatus for removing emboli during a carotid stenting procedure that enable filtering of emboli and reduced blood loss.

The foregoing objects of the present invention are accomplished by providing interventional apparatus comprising an arterial catheter, an occlusion balloon disposed on a guide wire, a venous return catheter, and, optionally, a blood filter and flow control valve disposed between the arterial and venous return catheters. The arterial catheter has proximal and distal ends, an aspiration lumen extending therebetween, an occlusion element disposed on the distal end, and a hemostatic port and blood outlet port disposed on the proximal end that communicate with the aspiration lumen. The aspiration lumen is sized so that an interventional instrument, e.g., an angioplasty catheter or stent delivery system, may be readily advanced therethrough to the site of a stenosis in either the ECA (proximal to the balloon) or the ICA.

In accordance with the principles of the present invention, the arterial catheter is illustratively disposed in the CCA proximal of the ICA/ECA bifurcation, the occlusion balloon on the guide wire is disposed in the ECA to occlude flow reversal from the ECA to the ICA, and the blood outlet port of the arterial catheter is coupled to the venous return catheter, with or without the blood filter and flow control valve disposed therebetween. Higher arterial than venous pressure, especially during diastole, coupled with the flow control valve permits controlled flow reversal in the ICA during an interventional procedure (other than when a dilatation balloon is inflated) to flush blood containing emboli from the vessel. The blood is filtered and reperfused into the body through the venous return catheter.

Methods of using the apparatus of the present invention are also provided.

BRIEF DESCRIPTION OF THE DRAWINGS

Further features of the invention, its nature and various advantages will be more apparent from the accompanying drawings and the following detailed description of the preferred embodiments, in which:

FIGS. 9A–9C are, respectively, detailed side-sectional views and a cross-sectional view of the distal end of yet another alternative interventional device of the present invention; and FIGS. 10A–10C illustrate a method of using the apparatus of FIG. 3 as adjunct to an emboli removal filter.

DESCRIPTION OF THE PREFERRED EMBODIMENTS

Figure 1A:
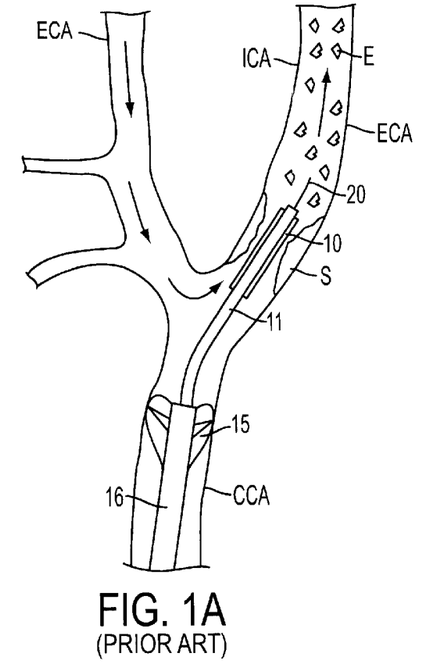
FIGS. 1A and 1B are schematic views of previously known emboli protection systems.
Figure 1B:
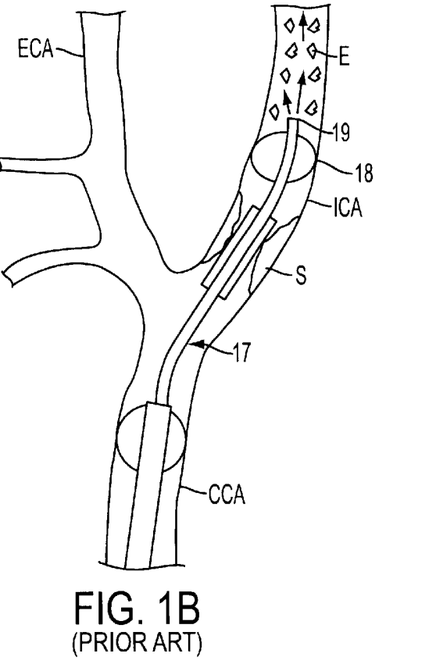

Referring to FIGS. 1A and 1B, drawbacks of previously known emboli removal catheters are described with reference to performing percutaneous angioplasty of stenosis S in common carotid artery CCA.

With respect to FIG. 1A, drawbacks associated with naturally-aspirated emboli removal systems, such as described in the above-mentioned patent to Solano and European Patent Publication, are described. No flow reversal is induced by those systems until after balloon 10 of angioplasty catheter 11 first is passed across the stenosis, inflated, and then deflated. However, applicant has determined that once member 15 of emboli removal catheter 16 is inflated, flow within the ECA reverses and provides antegrade flow into the ICA, due to the lower hemodynamic resistance of the ICA. Consequently, emboli E generated while passing guide wire 20 or catheter 11 across stenosis S may be carried irretrievably into the cerebral vasculature—before flow in the vessel is reversed and directed into the aspiration lumen of emboli removal catheter 16 by opening the proximal end of the aspiration lumen to atmospheric pressure. Furthermore, natural-aspiration may not remove an adequate volume of blood to retrieve even those emboli that have not yet been carried all the way into the cerebral vasculature.

In FIG. 1B, system 17 described in the above-mentioned patent to Imran is shown. As described hereinabove, deployment of distal balloon 18, and ejection of blood out of the distal end of the inner catheter, may dislodge emboli from the vessel wall distal to balloon 18. The introduction of antegrade flow through inner catheter 19 is expected only to exacerbate the problem by pushing the emboli further into the cerebral vasculature. Thus, while the use of positive suction in the Imran system may remove emboli located in the confined treatment field defined by the proximal and distal balloons, such suction is not expected to provide any benefit for emboli dislodged distal of distal balloon 18.

Figure 2:
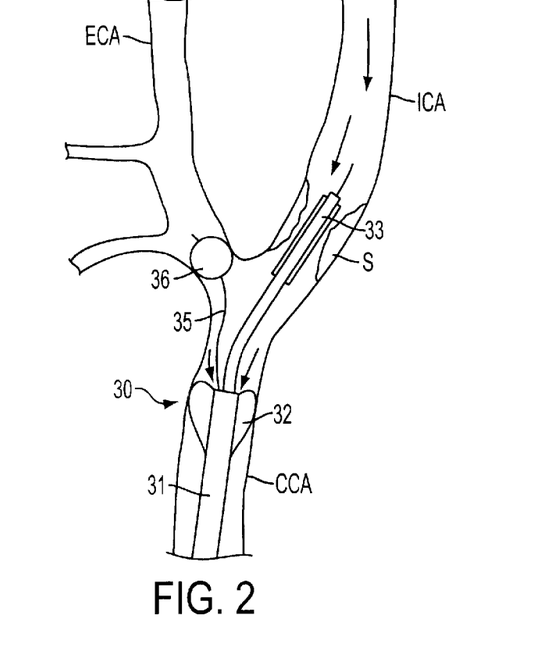
FIG. 2 is a schematic view of the emboli protection system of the present invention.

Referring now to FIG. 2, apparatus and methods of the present invention are described. Apparatus 30 comprises catheter 31 having an aspiration lumen and occlusion element 32, and guide wire 35 having inflatable balloon 36 disposed on its distal end. In accordance with the principles of the present invention, antegrade blood flow is stopped when both occlusion element 32 in the CCA and inflatable balloon 36 are deployed. Furthermore, the aspiration lumen of catheter 31 is connected to a venous return catheter (described hereinbelow) disposed, for example, in the patient's femoral vein. In this manner a substantially continuous flow of blood is induced between the treatment site and the patient's venous vasculature. Because flow through the artery is towards catheter 31, any emboli dislodged by advancing a guide wire or angioplasty catheter 33 across stenosis S causes the emboli to be aspirated by catheter 31.

Unlike the previously known naturally-aspirated systems, the present invention provides substantially continuous retrograde blood flow through the ICA while preventing blood from flowing retrograde in the ECA and antegrade into the ICA, thereby preventing emboli from being carried into the cerebral vasculature. Because the apparatus and methods of the present invention "recycle" emboli-laden blood from the arterial catheter through the blood filter and to the venous return catheter, the patient experiences significantly less blood loss.

Figure 3A:
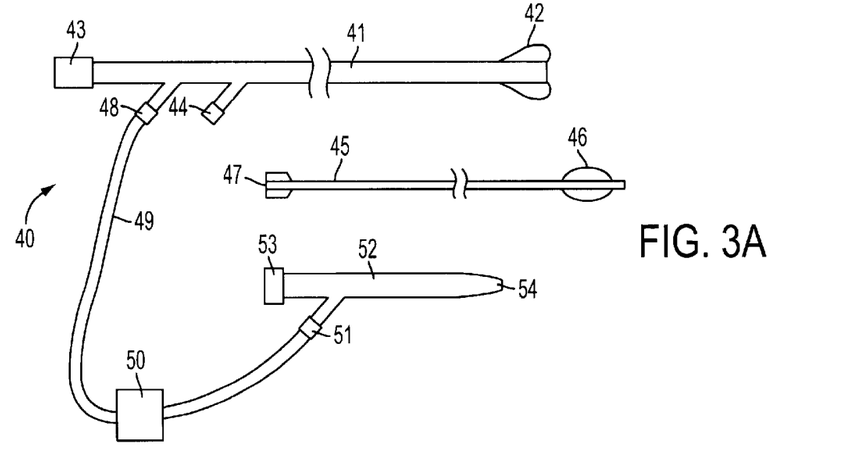
FIGS. 3A–3D are, respectively, a schematic view, and detailed side and sectional views of the distal end of an interventional device of the present invention.

Referring now to FIG. 3A, embolic protection apparatus 40 constructed in accordance with the principles of the present invention is described. Apparatus 40 comprises arterial catheter 41, guide wire 45, venous return line 52, tubing 49 and optional blood filter 50.

Catheter 41 includes distal occlusion element 42, proximal hemostatic port 43, e.g., a Touhy-Borst connector, inflation port 44, and blood outlet port 48. Guide wire 45 includes balloon 46 that is inflated via inflation port 47. Tubing 49 couples blood outlet port 48 to filter 50 and blood inlet port 51 of venous return line 52.

Guide wire 45 and balloon 46 are configured to pass through hemostatic port 43 and the aspiration lumen of catheter 41 (see FIGS. 3C and 3D), so that the balloon may be advanced into and occlude the ECA. Port 43 and the aspiration lumen of catheter 41 are sized to permit additional interventional devices, such as angioplasty balloon catheters, atherectomy devices and stent delivery systems to be advanced through the aspiration lumen when guide wire 45 is deployed.

Guide wire 45 preferably comprises a small diameter flexible shaft having an inflation lumen that couples inflatable balloon 46 to inflation port 47. Inflatable balloon 46 preferably comprises a compliant material, such as described hereinabove with respect to occlusion element 42 of emboli removal catheter 41.

Venous return line 52 includes hemostatic port 53, blood inlet port 51 and a lumen that communicates with ports 53 and 51 and tip 54. Venous return line 52 may be constructed in a manner per se known for venous introducer catheters. Tubing 49 may comprise a suitable length of a biocompatible material, such as silicone. Alternatively, tubing 49 may be omitted and blood outlet port 48 of catheter 41 and blood inlet port 51 of venous return line 52 may be lengthened to engage either end of filter 50 or each other.

Figure 3B:
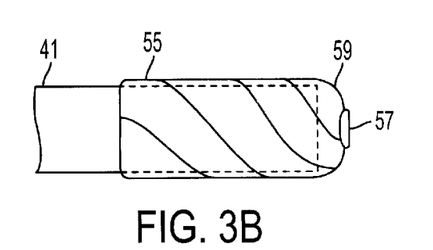
Figure 3C:
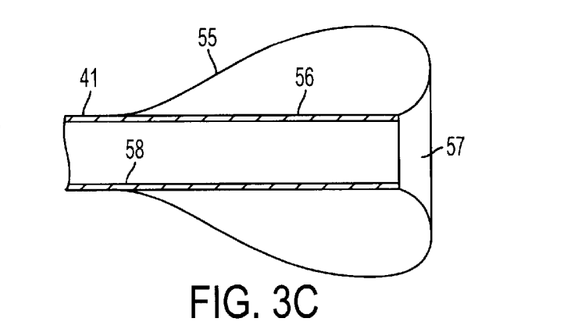

With respect to FIGS. 3B and 3C, distal occlusion element 42 comprises expandable bell or pear-shaped balloon 55. In accordance with manufacturing techniques which are known in the art, balloon 55 comprises a compliant material, such as polyurethane, latex or polyisoprene which has variable thickness along its length to provide a bell-shape when inflated. Balloon 55 is affixed to distal end 56 of catheter 41, for example, by gluing or a melt-bond, so that opening 57 in balloon 55 leads into aspiration lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

Figure 3D:
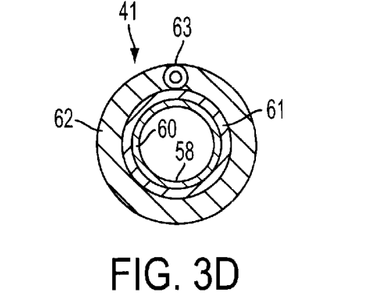

As shown in FIG. 3D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 55. In a preferred embodiment of catheter 41, the diameter of lumen 58 is 7 Fr, and the outer diameter of the catheter is approximately 9 Fr.

Figure 4A:
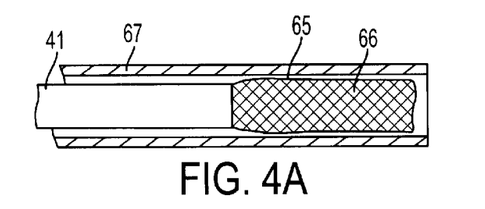
FIGS. 4A and 4B are views of the distal end of an alternative interventional device suitable for use in the system of the present invention.
Figure 4B:
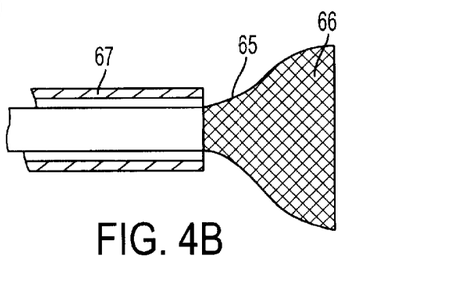

Referring now to FIGS. 4A and 4B, an alternative embodiment of occlusion element 42 of the system of FIG. 3A is described. In FIGS. 4A and 4B, occlusion element 42 of emboli removal catheter 41 comprises self-expanding wire basket 65 covered with elastomeric polymer 66, such as latex, polyurethane or polyisoprene. Alternatively, a tightly knit self-expanding wire mesh may be used, with or without an elastomeric covering.

Catheter 41 is surrounded by movable sheath 67. Catheter 41 is inserted transluminally with sheath 67 in a distalmost position, and after basket 65 has been determined to be in a desired position proximal to a stenosis, sheath 67 is retracted proximally to cause basket 65 to deploy. Upon completion of the procedure, basket 65 is again collapsed within sheath 67 by moving the sheath to its distalmost position. Operation of the system of FIG. 3A using the emboli removal catheter of FIGS. 4A and 4B is similar to that described hereinbelow for FIGS. 5A–5D, except that the occlusion element self-expands when sheath 67 is retracted, rather than by infusing an inflation medium to balloon 55.

Figure 5A:
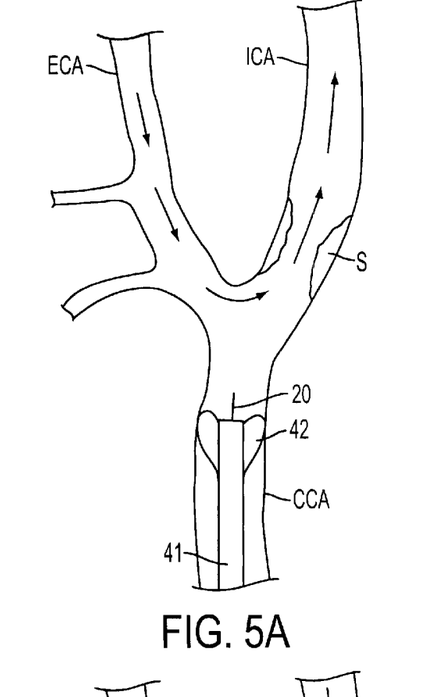
FIGS. 5A–5D illustrate a method of using the system of FIG. 3 in accordance with the principles of the present invention.

Referring now to FIGS. 5A–5D, use of the apparatus of FIGS. 3 in accordance with the methods of the present invention is described. In FIGS. 5, stenosis S is located in internal carotid artery ICA above the bifurcation between the internal carotid artery ICA and the external carotid artery ECA. In a first step, catheter 41 is inserted, either percutaneously and transluminally or via a surgical cut-down, to a position proximal of stenosis S, without causing guide wire 45 to cross the stenosis. Balloon 55 of distal occlusion element 42 is then inflated, preferably with a radiopaque contrast solution, via inflation port 44. As seen in FIG. 5A, this creates reversal of flow from the external carotid artery ECA into the internal carotid artery ICA.

Figure 5B:
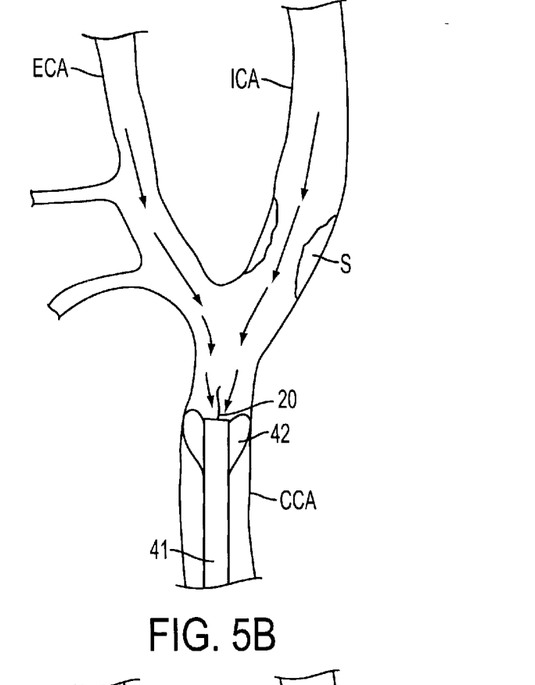

Venous return line 52 then is introduced into the patient's femoral vein, either percutaneously or via a surgical cut-down. Filter 50 is then coupled between blood outlet port 48 of catheter 41 and blood inlet port 51 of venous return line 52 using tubing 49, and any air is removed from the line. Once this circuit is closed, negative pressure in the venous catheter during diastole will establish a low rate continuous flow of blood through aspiration lumen 58 of catheter 41, as seen in FIG. 5B, to the patient's vein via venous return line 52.

This low rate continuous flow due to the difference between venous pressure and arterial pressure will continue throughout the interventional procedure. Specifically, blood passes through aspiration lumen 58 and blood outlet port 48 of catheter 41, through biocompatible tubing 49 to filter 50, and into blood inlet port 51 of venous return line 52, where it is reperfused into the remote vein. Filtered emboli collect in filter 50 and may be studied and characterized upon completion of the procedure.

Continuous blood flow (except during inflation of any dilatation instruments) with reperfusion in accordance with the present invention provides efficient emboli removal with significantly reduced blood loss. Alternatively, filter 50 may be omitted, in which case emboli removed from the arterial side will be introduced into the venous side, and eventually captured in the lungs. Because of a low incidence of septal defects, which could permit such emboli to cross-over to the left ventricle, the use of filter 50 is preferred.

Figure 5C:
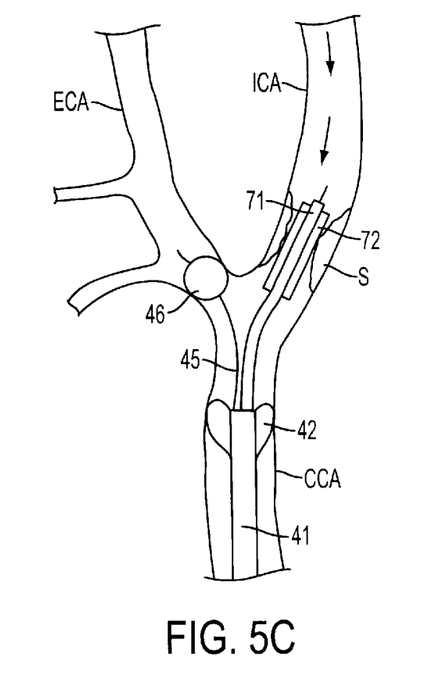

Referring to FIG. 5C, with balloon 55 of occlusion element 42 inflated and a retrograde flow established in the ICA, guide wire 45 and balloon 46 are advanced through aspiration lumen 58. When balloon 46 is disposed within the ECA, as determined, e.g., using a fluoroscope and a radiopaque inflation medium injected into balloon 46, balloon 46 is inflated. Occlusion of the ECA prevents the development of reverse flow in the ECA from causing antegrade flow in the ICA. Another interventional instrument, such as conventional angioplasty balloon catheter 71 having balloon 72, is loaded through hemostatic port 43 and aspiration lumen 58 and positioned within the stenosis. Hemostatic port 43 is closed and instrument 71 is actuated to disrupt the plaque forming stenosis S.

Figure 5D:
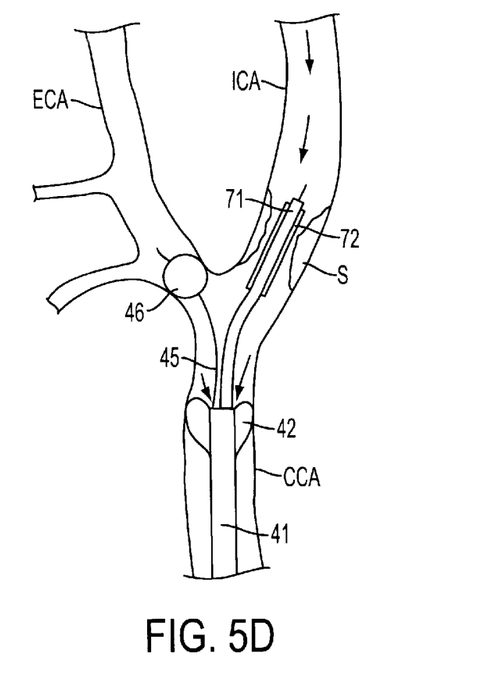

As seen in FIG. 5D, upon completion of the angioplasty portion of the procedure using catheter 71, balloon 72 is deflated. Throughout the procedure, except when the dilatation balloon is fully inflated, the pressure differential between the blood in the ICA and the venous pressure causes blood in ICA to flow in a retrograde direction in the ICA into aspiration lumen 58 of emboli removal catheter 41, thereby flushing any emboli from the vessel. The blood is filtered and reperfused into the patient's vein.

Optionally, increased volumetric blood flow through the extracorporeal circuit may by achieved by attaching an external pump, such as a roller pump, to tubing 49. If deemed beneficial, the external pump may be used in conjunction with device 40 at any point during the interventional procedure. Instrument 71, guide wire 45, emboli removal catheter 41, and venous return line 52 are then removed from the patient, completing the procedure.

As set forth above, the method of the present invention protects against embolization, first, by preventing the reversal of blood flow from the ECA to the ICA when distal occlusion element 42 is inflated, and second, by providing continuous, low volume blood flow from the carotid artery to the remote vein in order to filter and flush any emboli from the vessel and blood stream. Advantageously, the method of the present invention permits emboli to be removed with little blood loss, because the blood is filtered and reperfused into the patient. Furthermore, continuous removal of blood containing emboli prevents emboli from migrating too far downstream for aspiration.

Figure 6A:
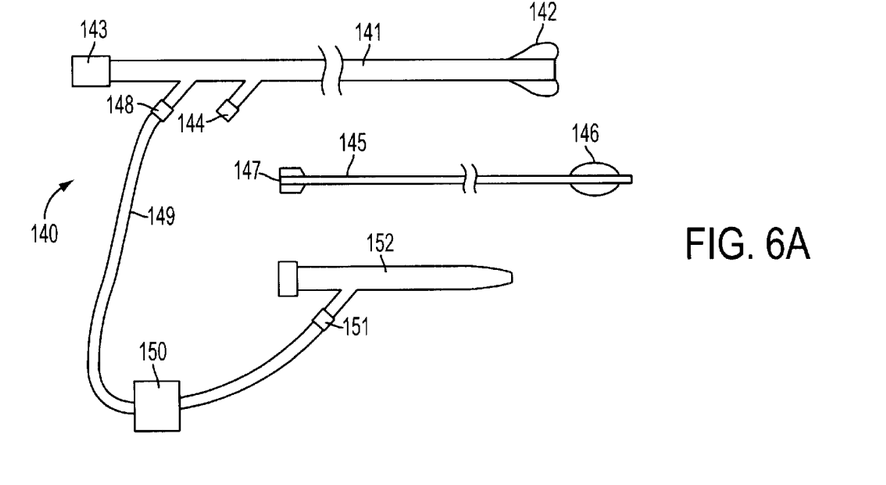
FIGS. 6A and 6B are, respectively, a schematic view and a cross-sectional view of an alternative embodiment of the device of FIGS. 3.

Referring now to FIG. 6, apparatus 140 constructed in accordance with the present invention is described. Apparatus 140 is an alternative embodiment of apparatus 40 described hereinabove and comprises arterial catheter 141 having distal occlusion element 142, proximal hemostatic port 143, inflation port 144 and blood outlet port 148. Guide wire 145 includes balloon 146 that is inflated via inflation port 147. Biocompatible tubing 149 couples blood outlet port 148 to filter 150 and to blood inlet port 151 of venous return line 152. Arterial catheter 141, guide wire 145, venous return line 152 and tubing 149 are constructed as described hereinabove, except as noted below.

Figure 6B:
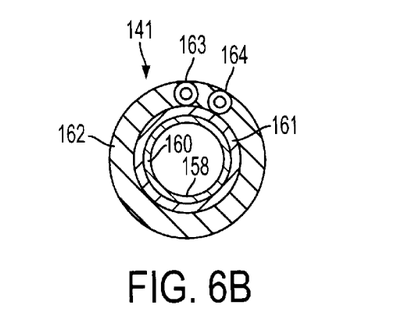

Guide wire 145 and balloon 146 are configured to pass through guide wire lumen 164 of catheter 141 (see FIG. 6B), so that the balloon may be advanced into and occlude the ECA. Additionally, catheter 141 comprises aspiration lumen 158 which is sized to permit interventional devices, such as angioplasty balloon catheters, atherectomy devices and stent delivery systems to be advanced through port 143 and the aspiration lumen. As shown in FIG. 6B, one difference between catheters 41 and 141 is the method of advancing the guide wire through the catheter: guide wire 45 is advanced through the aspiration lumen of catheter 41, whereas guide wire 145 is advanced through separate guide wire lumen 164 of catheter 141.

Catheter 141 preferably is constructed from inner layer 160 of low-friction material, such as polytetrafluoroethylene ("PTFE"), covered with a layer of flat stainless steel wire braid 161, and polymer cover 162 (e.g., polyurethane, polyethylene, or PEBAX). Inflation lumen 163 is disposed within polymer cover 162 and couples inflation port 144 to occlusion element 142. Guide wire lumen 164 also is disposed within polymer cover 142, and is sized to permit guide wire 145 and balloon 146 to pass therethrough. In a preferred embodiment of catheter 141, the diameter of inflation lumen 163 is 0.014", the diameter of guide wire lumen 164 is 0.020", and the diameter of lumen 158 is 7 Fr. To retain an outer catheter diameter in the referred embodiment of approximately 9 Fr., the thickness of the catheter wall varies around the circumference from a maximum of 0.026" at the location of guide wire lumen 164 to a minimum of 0.005" 180 degrees away.

Figure 7A:
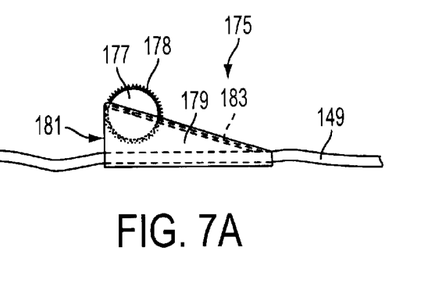
FIGS. 7A and 7B are side views of a flow control valve for use with the venous return line of the present invention shown, respectively, in an open position and a closed position.
Figure 7B:
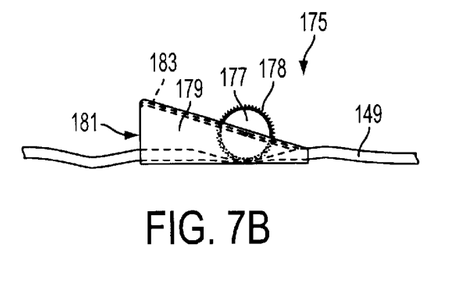

With reference to FIGS. 7A and 7B, a flow control valve for use with the venous return line is described. Flow control valve 175 is illustratively shown connected to a portion of biocompatible tubing 149 of FIG. 6A. Valve 175 comprises pinch wheel 177 and member 179. Member 179 comprises channel 181 and inclined track 183. Pinch wheel 177 includes teeth 178 and is configured to pass through channel 181 along track 183. Channel 181 is also configured to receive tubing 149. Pinch wheel 177 may move along track 183 from a first position, shown in FIG. 7A, in which it does not compress tubing 149, to a user-selected second position, shown in FIG. 7B, at which tubing 149 is compressed a user-selected degree to reduce or stop flow through tubing 149.

When used in conjunction with the apparatus of the present invention, valve 175 allows a selective degree of constriction to be applied to the venous return line. Thus, valve 175 provides selective control over the amount of reverse flow from the carotid artery to the femoral vein. Some patients may tolerate cessation of antegrade flow in the ICA, or a gentle reversal of flow, but may not tolerate the brain ischemia associated with full reversal of flow. Valve 175 therefore allows a slow, gentle reversal—or even cessation—of antegrade flow to be established in the ICA. As long as flow is stopped or slightly reversed, emboli will not travel to the brain. Aspiration prior to deflation of the distal occlusion element ensures that emboli sitting in the carotid or within the sheath are removed.

Figure 8A:
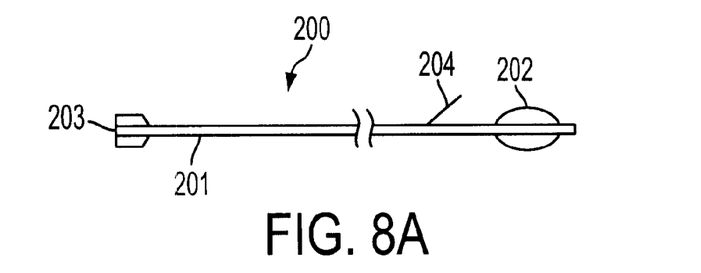
FIGS. 8A and 8B are, respectively, a schematic view of an alternative embodiment of the guide wire balloon element of the device of FIG. 3, and a method of using that device.

Referring now to FIG. 8, an alternative embodiment of the guide wire occlusion apparatus of the present invention is described. Occlusion apparatus 200 comprises guide wire 201, occlusion balloon 202, inflation lumen 203, and wedge 204. Wedge 204 may comprise a resilient material, such as a polymer or resilient wire, and reduces the risk that balloon 202 will snag on a stent that extends beyond the bifurcation of the ICA and ECA.

For the reasons described hereinabove, it is desirable when performing a stenting procedure in the ICA to occlude the ECA, to prevent flow reversal from the ECA and into the ICA. Accordingly, an occlusion balloon on a guide wire is placed in the ECA and inflated to block that artery. A stent then may be placed in the ICA to ensure proper blood flow to the ICA. It is often desirable, however, for such stents to extend beyond the bifurcation between the ECA and the ICA. Consequently, when the occlusion balloon on the guide wire is deflated and withdrawn from the ECA, there is a risk that the balloon may snag the stent. In such cases, emergency surgery is often required to remove the balloon.

Figure 8B:
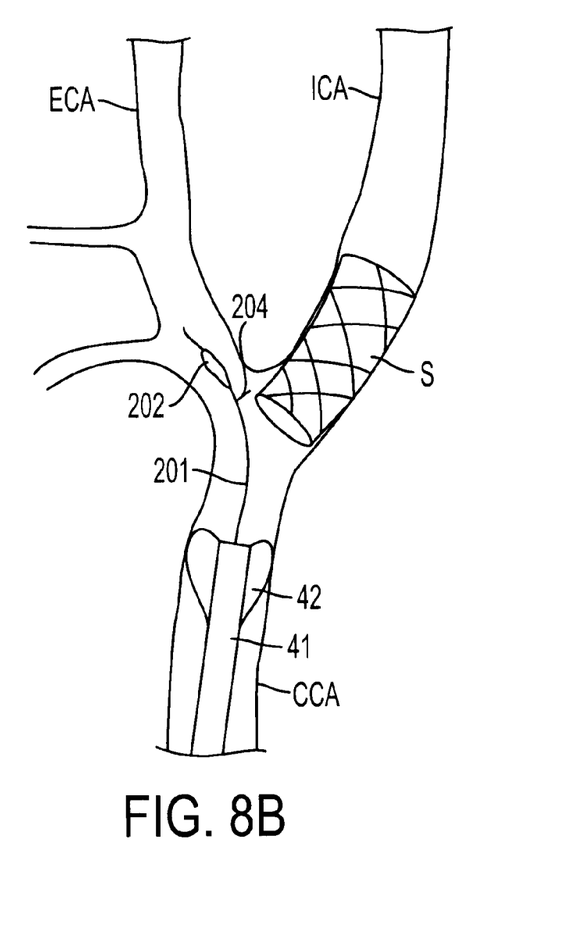

Referring now to FIG. 8B, occlusion apparatus 200 is illustratively shown in conjunction with catheter 41. Stent S extends beyond the bifurcation between the ECA and the ICA and into the CCA. Balloon 202 is deflated and positioned for retrieval. Because balloon 202 is disposed on guide wire 201 instead of a traditional, larger diameter balloon catheter, its cross-sectional diameter is significantly reduced, and thus the risk that the balloon will snag on stent S is reduced. Resilient wedge 204 further reduces this risk by urging the balloon outward away from the stent during retrieval of guide wire 201 and balloon 202. Alternatively, a separate sheath may be advanced over guide wire 201 and occlusion balloon 202 to surround those components, and therefore reduce the risk that the occlusion balloon or guide wire will snag the stent.

With reference to FIG. 9, the distal end of yet another alternative interventional device suitable for use in the system of the present invention is described. Because balloon 55 of FIG. 3A is attached to a stepped portion of catheter 41, apparatus 40 requires use of a larger diameter introducer sheath compared to a standard guide catheter without such a balloon. At the point of attachment of balloon 55, however, catheter 41 does not require the torque, strength, or stiffness of a regular guide catheter. Balloon 55 has its own inflation means, and, in use, the tip of catheter 41 does not intubate an artery.

As seen in FIGS. 9A and 9B, distal occlusion element 210 comprises expandable bell or pear-shaped balloon 212. Balloon 212 is similar to balloon 55. In accordance with manufacturing techniques which are known in the art, balloon 212 comprises a compliant material, such as polyurethane, latex or polyisoprene which has variable thickness along its length to provide a bell-shape when inflated. Balloon 212 is affixed to reduced-thickness distal region 216 of arterial catheter 214, for example, by gluing or a melt-bond, so that opening 218 in balloon 212 leads into aspiration lumen 220 of catheter 214. Balloon 212 preferably is wrapped and heat treated during manufacture so that distal portion 222 of the balloon extends beyond the distal end of catheter 214 and provides an atraumatic tip or bumper for the catheter.

As shown in FIG. 9C, catheter 214 preferably comprises inner layer 232 of low-friction material, such as polytetrafluoroethylene ("PTFE"), covered with a layer of flat stainless steel wire braid 234 and polymer cover 236 (e.g., polyurethane, polyethylene, or PEBAX). Inflation lumen 238 is disposed within polymer cover 236 and couples an inflation port (not shown) to balloon 212. In a preferred embodiment of catheter 214, the diameter of lumen 220 is 7 Fr, and the outer diameter of the catheter is approximately 9 Fr.

Arterial catheter 214 is similar to catheter 41 of FIG. 3, except at reduced-thickness distal region 216. Distal region 216 preferably achieves its reduced thickness by omission of wire braid 234 in that region. Thus, when balloon 212 is deflated, the composite delivery profile of distal end 216 and balloon 212 is the substantially same as or smaller than the delivery profile of the remainder of catheter 214. Preferably, the device has a delivery profile of approximately 9 Fr (see FIG. 9A). The diameter of lumen 230 remains the same along the entire length of catheter 214, preferably around 7 Fr. Catheter 214 therefore requires an introducer sheath of no larger diameter than those required by a standard guide catheter.

With reference now to FIGS. 10A–10C, the apparatus of the present invention also may be used as an adjunct against embolization when used with a distally deployed embolic filter. Embolic filter 250 is illustratively shown in conjunction with catheter 41, and comprises guide wire 252 and expandable mesh 254.

Catheter 41 may provide adjunct protection in a variety of ways. For example, as depicted in FIG. 10A, reverse flow through catheter 41 may be established, as described hereinabove, during deployment of filter 250 to capture emboli E generated while passing filter 250 across stenosis S. Alternatively, if, after deployment, filter 250 becomes overly filled with emboli E, reverse flow may be established to provide a pressure differential that aspirates emboli from the filter and into catheter 41, as depicted in FIG. 10B. Also, in the event filter 250 fails, for example, during retrieval, reverse flow may be established to prevent emboli E or fragments of the filter from being carried downstream, as seen in FIG. 10C. In addition to catheter 41, the filter also may be used in conjunction with balloon 46 so that blood flow is not unnecessarily reversed in, for example, the ECA when emboli E are generated in the ICA.

As will of course be understood, the apparatuses of the present invention may be used in locations other than the carotid arteries. They may, for example, be used in the coronary arteries, or in any other locations deemed useful.

While preferred illustrative embodiments of the invention are described above, it will be apparent to one skilled in the art that various changes and modifications may be made. The appended claims are intended to cover all such changes and modifications that fall within the true spirit and scope of the invention.

What is claimed is:

1. Apparatus for removing emboli during an angioplasty or stenting procedure the apparatus comprising:

a catheter having proximal and distal ends, an aspiration lumen and a guide wire lumen, each of the aspiration lumen and guide wire lumen extending from the proximal end to the distal end, and a blood outlet port in communication with the aspiration lumen, the catheter adapted to be disposed in a patient's carotid artery;

an occlusion element disposed on the distal end of the catheter and having an opening that communicates with the aspiration lumen, the occlusion element having a contracted state suitable for transluminal insertion and an expanded state wherein the occlusion element occludes antegrade flow in the artery;

a venous return catheter having proximal and distal ends, a lumen extending therethrough, and a blood inlet port in communication with the lumen;

tubing that couples the blood outlet port to the blood inlet port;

a flow control valve coupled between the blood outlet port and blood inlet port; and a wire having a distal end and a balloon disposed on the distal end, wherein the wire and balloon are sized to pass through the guide wire lumen of the catheter.

2. The apparatus of claim 1 further comprising a blood filter coupled between the blood outlet port and the blood inlet port.

3. The apparatus of claim 1 wherein the occlusion element is an inflatable member.

4. The apparatus of claim 3 wherein the inflatable element has a pear-shape with a wall thickness that varies along the length of the inflatable member.

5. The apparatus of claim 3 wherein a portion of the pear-shaped inflatable member extends beyond the distal end of the catheter in the contracted position and forms an atraumatic bumper.

6. The apparatus of claim 3 wherein a portion of the pear-shaped inflatable member extends beyond the distal end of the catheter in the contracted position and forms an atraumatic bumper.

7. The apparatus of claim 1 wherein the catheter comprises:

a non-stick tubular member;

a layer of wire braid disposed surrounding the non-stick tubular member; and a layer of thermoplastic polymer disposed on the layer of wire braid.

8. The apparatus of claim 7 wherein the layer of wire braid is omitted in a distal region of the catheter.

9. The apparatus of claim 1 wherein the apparatus has a substantially uniform cross sectional diameter when the occlusion element is in the contracted state.

10. The apparatus of claim 1 further comprising a pump that removes blood through the catheter and reperfuses blood via the venous return catheter.

11. The apparatus of claim 1 further comprising a resilient wedge affixed to the wire proximal of the balloon to reduce snagging of the balloon following a stenting procedure.

12. Apparatus for removing emboli during an angioplasty or stenting procedure and a balloon disposed on the distal end, the apparatus comprising:
 a catheter having a proximal end and a distal end, an aspiration lumen and a guide wire lumen, each of the aspiration lumen and the guide wire lumen extending from the proximal to the distal end, and a blood outlet port in communication with the aspiration lumen, the catheter adapted to be disposed in a patient's carotid artery;
 an occlusion element disposed on the distal region of the catheter and having an opening that communicates with the aspiration lumen, the occlusion element having a contracted state suitable for transluminal insertion and an expanded state wherein the occlusion element occludes antegrade flow in the artery;
 a venous return catheter having proximal and distal ends, a lumen extending therethrough, and a blood inlet port in communication with the lumen;
 tubing that couples the blood outlet port to the blood inlet port; and a wire having a distal end and a balloon disposed on the distal end, wherein the wire and balloon are sized to pass through the guide wire lumen of the catheter.

13. The apparatus of claim 12 further comprising a flow control valve coupled between the blood outlet port and blood inlet port.

14. The apparatus of claim 12 further comprising a blood filter coupled between the blood outlet port and the blood inlet port.

15. The apparatus of claim 12 wherein the occlusion element is an inflatable member.

16. The apparatus of claim 15 wherein the inflatable element has a pear-shape with a wall thickness that varies along the length of the inflatable member.

17. The apparatus of claim 12 wherein the catheter comprises:
 a non-stick tubular member;
 a layer of wire braid disposed surrounding the non-stick tubular member; and
 a layer of thermoplastic polymer disposed on the layer of wire braid.

18. The apparatus of claim 12 wherein the apparatus has a substantially uniform cross sectional diameter when the occlusion element is in the contracted state.

19. The apparatus of claim 12 further comprising a pump that removes blood through the catheter and reperfuses blood via the venous return catheter.

* * * * *